United States Patent [19]

Whittle

[11] Patent Number: 4,788,349
[45] Date of Patent: Nov. 29, 1988

[54] HALOGENATED DIPHENYL ETHER DERIVATIVES

[75] Inventor: Alan J. Whittle, Aldershot, England

[73] Assignee: Imperial Chemical Industries PLC, London, England

[21] Appl. No.: 52,969

[22] Filed: May 22, 1987

[30] Foreign Application Priority Data

Jun. 9, 1986 [GB] United Kingdom ............... 8614002

[51] Int. Cl.$^4$ .......................................... C07C 43/225
[52] U.S. Cl. ..................... 568/639; 570/127
[58] Field of Search ......................................... 568/639

[56] References Cited

U.S. PATENT DOCUMENTS 3,257,471 6/1966 Hennessy ........................... 568/639
4,288,386 9/1981 Soula et al. ........................ 568/639

FOREIGN PATENT DOCUMENTS 0057384 8/1982 European Pat. Off. .
0238272 9/1987 European Pat. Off. .
3200431 7/1983 Fed. Rep. of Germany ...... 568/639
1327189 4/1963 France ............................ 568/639
2539411 1/1983 France .
1561575 2/1980 United Kingdom .

OTHER PUBLICATIONS

Wray et al., J. Chem. Soc. Perkin II, 1976, pp. 1307-1312, Chem. Abstract, vol. 64, #2032e, (1966).
Analytical Chemistry, vol. 33, No. 6, (May, 1961), pp. 657, 689, 690.

Primary Examiner—James H. Reamer
Attorney, Agent, or Firm—Cushman, Darby & Cushman

[57] ABSTRACT

Compounds of the Formula:

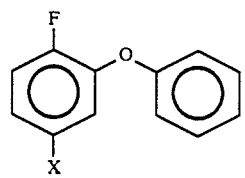

wherein X is selected from bromine and chlorine useful as intermediates in the preparation of insecticidal compounds.

3 Claims, No Drawings

HALOGENATED DIPHENYL ETHER DERIVATIVES

This invention relates to novel halogenated diphenyl ethers, useful as intermediates in the preparation of insecticidal compounds, and to methods and intermediates for their preparation.

In a first aspect, the invention provides novel compounds of formula (I):

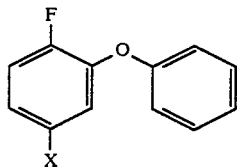

wherein X is selected from bromine and chlorine. The specific compounds according to the invention are:
4-bromo-1-fluoro-2-phenoxybenzene, and
4-chloro-1-fluoro-2-phenoxybenzene The compounds of formula (I) are particularly useful as intermediates for the preparation of insecticides. UK patent Specification No. 1,561,575 discloses the use of 1-bromo-3-phenoxybenzene as an intermediate in the preparation of insecticidally active alpha-trifluoromethyl-3-phenoxy-benzyl esters of carboxylic acids. Use of the compound of formula (I) wherein X is bromine in a manner analogous to that described in UK patent Specification No. 1,561,575 provides alpha-trifluoromethyl-3-phenoxy-4-fluorobenzyl alcohol. This process is illustrated in Scheme I.

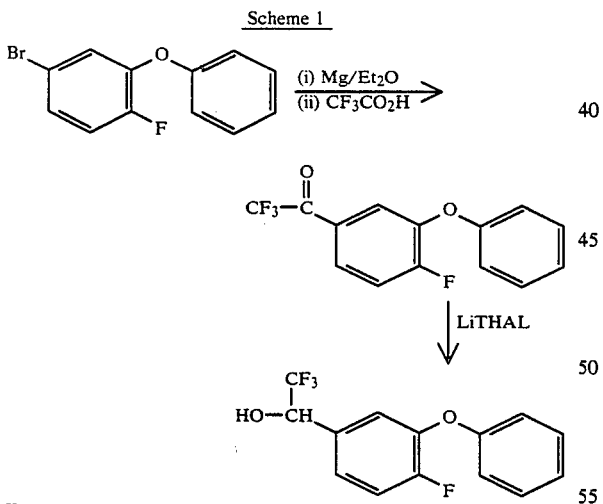

Key:
LiTHAL = lithium aluminium hydride
Et$_2$O = Diethyl ether

The compound of formula (I) wherein X is bromine may also be used in the preparation of 4-fluoro-3-phenoxybenzaldehyde, a useful intermediate in the preparation of insecticidal compounds, for example 4-fluoro-3-phenoxybenzyl esters of cyclopropanecarboxylic acids and alpha-substituted derivatives thereof. One method of preparing 4-fluoro-3-phenoxybenzaldehyde follows the method of Olah and Arvanaghi, Angewandte Chemie, International Edition, 20, p 878, 1981 and is illustrated in Scheme II.

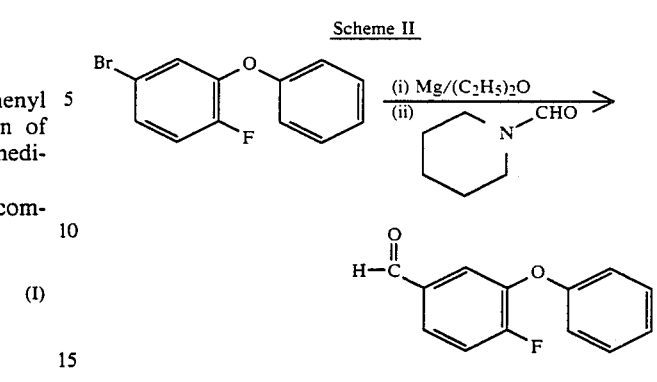

4-Fluoro-3-Phenoxybenzaldehyde may also be prepared from 4-bromo-1-fluoro-2-phenoxybenzene by the method of Einhorn and Luche, Tetrahedron Letters, 27, p 1791, 1986, as illustrated in Scheme III:

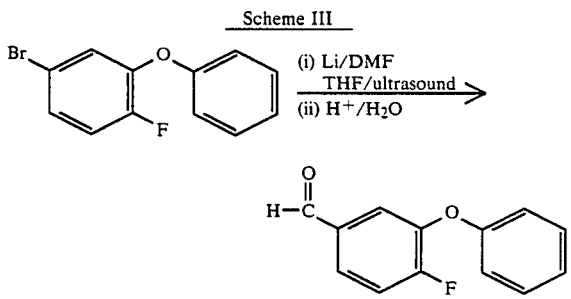

Key:
DMF = N,N—Dimethylformamide
THF = Tetrahydrofuran

4-Fluoro-3-phenoxybenzaldehyde is a useful intermediate in the preparation of 4-fluoro-3-phenoxybenzyl alcohol and its alpha-substituted derivatives, and insecticidal esters thereof. An example of its use is in the preparation of alpha-cyano-4-fluoro-3-phenoxybenzyl 3-(2-chloro-3,3,3-trifluoroprop-1-en-1-yl)-2,2-dimethylcyclopropanecarboxylate, according to the method described in UK patent application No. 2,161,804A. This process is illustrated in Scheme IV.

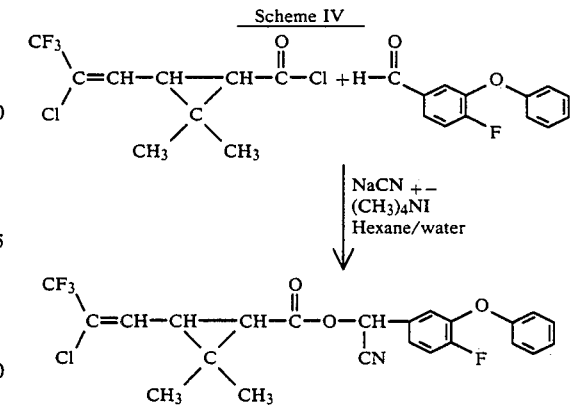

A further use of the compounds of formula (I) is in the preparation of compounds of formula (II), wherein R represents alkyl, useful as intermediates in the preparation of the insecticidal compounds described in the applicants' copending UK patent application No. 8703741.

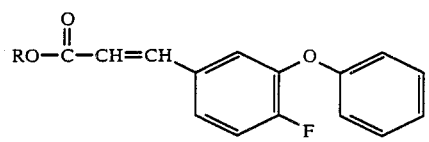  (II)

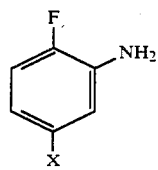  (III)

The compounds of formula (II) may be prepared from the compounds of formula (I) by the Heck reaction, using, for example, the method of Jeffery, Chemical Communications, 1984, p 1287. The preparation of methyl 3-(4-fluoro-3-phenoxyphenyl)propenoate from 4-bromo-1-fluoro-2-phenoxybenzene, and the subsequent conversion to 1,1,1-trifluoro-2-(4-ethoxyphenyl)-5-(4-fluoro-3-phenoxyphenyl)pentane, a compound which is disclosed in UK patent application No. 8703741, is illustrated in Scheme V.

In a further aspect, the invention provides a first process for preparing the compounds of formula (I), which comprises as a first step the diazotisation of 2-fluoro-5-haloanilines of formula (III):

wherein X is selected from bromine and chlorine, followed by the addition of the resultant diazonium salt solution to a cooled solution of an alkali metal iodide, for example, potassium iodide. This process leads to the formation of 4-halo-1-fluoro-2-iodobenzenes of formula (IV):

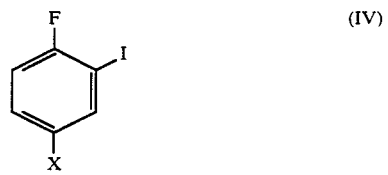  (IV)

The compounds of formula (IV) may then be converted to the compounds of formula (I) by reaction with phenol in the presence of a strong base and an Ullmann catalyst, such as copper or a copper salt, for example cuprous chloride. This process is illustrated, by way of example, in Scheme VI.

Scheme V

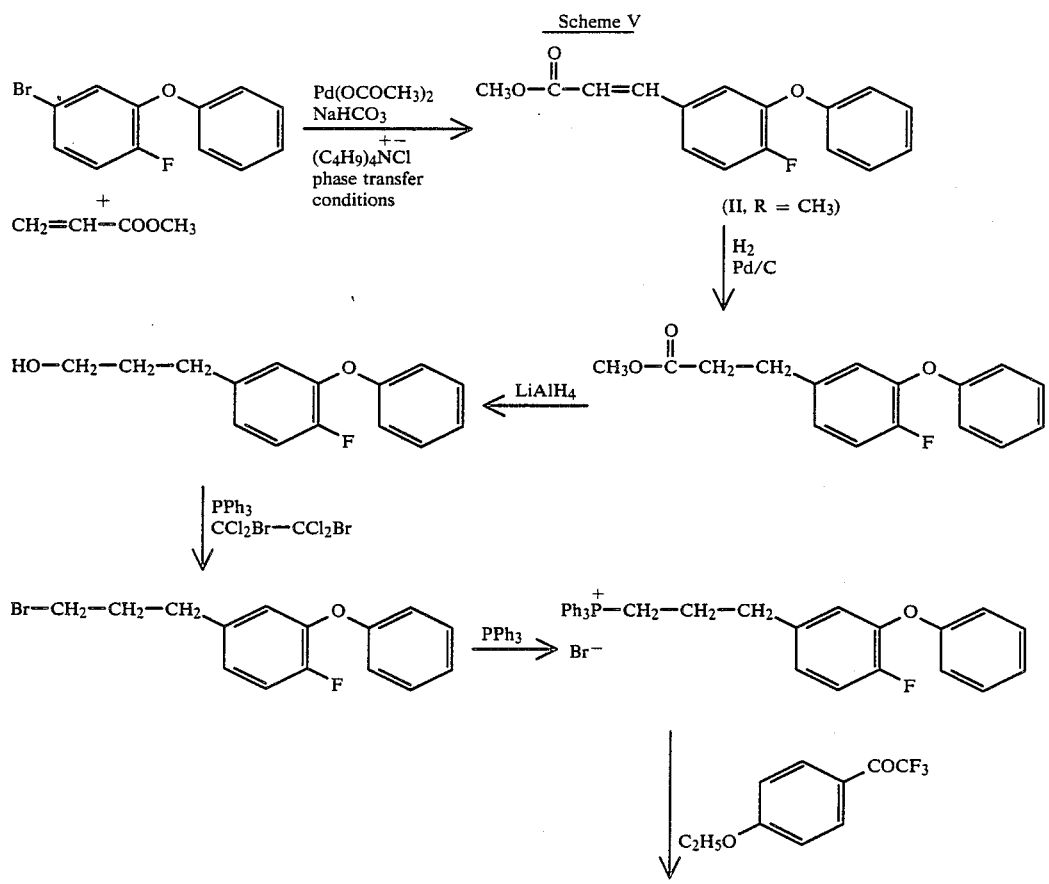

-continued
Scheme V

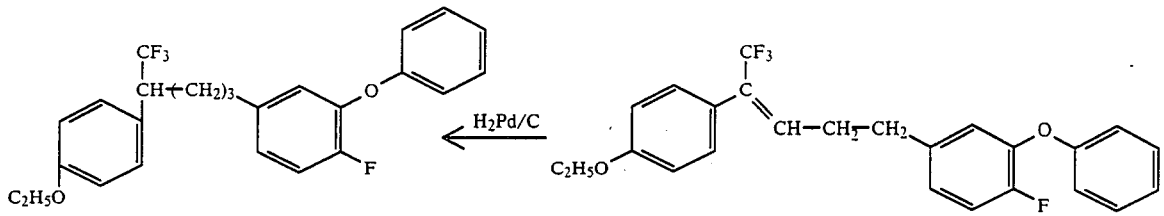

Scheme VI

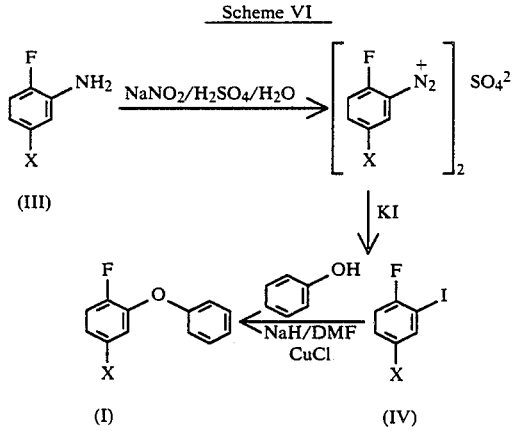

The 4-halo-1-fluoro-2-iodobenzenes of formula (IV) are believed to be novel. In a further aspect, therefore, the invention provides compounds of formula (IV), wherein X is selected from bromine and chlorine.

The compounds of formula (I) wherein X is bromine may also be prepared from 4-fluoro-3-phenoxybenzaldehyde. In a further aspect therefore, the invention provides a second process for the preparation of the compounds of formula (I), in which 4-fluoro-3phenoxybenzaldehyde is first oxidised to 4-fluoro-3-phenoxybenzoic acid, for example by the action of sodium periodate in the presence of ruthenium trichloride, using the method of Carlsen and Sharpless, Journal of Organic Chemistry, 46, 3936, 1981. The acid is then converted to the acid chloride deriviative using, for example, thionyl chloride. 4-Bromo-1-fluoro-2-phenoxybenzene may then be obtained from the acid chloride by reaction with bromothrichloromethane in the presence of an alkali metal salt of 2-pyridinethiol 1-oxide and a radical initiator using the method illustrated by Barton et al, Tetrahedron Letters, 24, 4979, 1983; Tetrahedron Letters, 26, 5939, 1985. This process is illustrated in Scheme VII.

Scheme VII

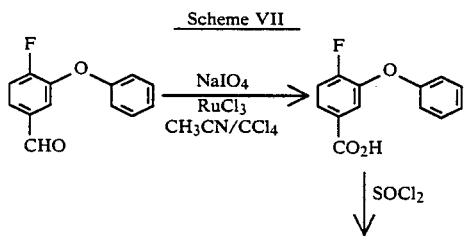

-continued
Scheme VII

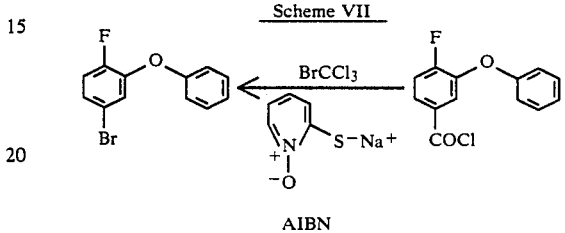

Key:
AIBN = α,α′azo-bis-isobutyronitrile

Further details of the processes of the invention are given in the following examples.

In the Examples the products were usually identified and characterised by means of Nuclear Magnetic Resonance spectroscopy and infra red spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liquid Chromatography (GLC) retention times were determined on a Hewlett Packard 5890 Gas Chromatograph, using a Chromopak C.P. Sil 5 C.B. column of 12.5M length and 0.2 mm internal diameter. Unless otherwise stated, the injection temperature was 100° C., and a temperature gradient of 15° C./minute employed, up to a maximum temperature of 280° C., maintained for 4 minutes. The carrier gas was helium at a column head pressure maintained at 11 psi. Alternative injection and maximum temperatures are indicated in the Examples where appropriate.

$^1$H Nuclear Magnetic Resonance (NMR) spectrometry was performed at a frequency of 270 MHz on a Jeol FX 270 NMR spectrometer, unless otherwise indicated. 90 MHz, 60 MHz and 400 MHz $^1$H NMR spectrometry were performed using Jeol FX 90Q, Jeol PMX 60SI and Jeol GX400 spectrometers respectively.

$^{19}$F NMR spectrometry was performed on a Jeol FX900 spectrometer at a frequency of 84.26 MHz. All NMR shift values are quoted in ppm relative to a standard (TMS or CFCl$_3$).

Molecular Ion (M+) peaks were determined on one of three mass spectrometers: Jeol DX303, Kratos MS80 or Hewlett Packard HP 5992.

EXAMPLE 1

This Example illustrates the preparation of 4-bromo-1-fluoro-2-iodobenzene.

A solution of sodium nitrite (1.71 g) in water (4 cm$^3$) was added dropwise to a stirred mixture of 5-bromo-2fluoroaniline (4.5 g), water (15 cm$^3$), ice (15 g) and concentrated sulphuric acid (1.8 cm$^3$) at a temperature maintained at 0°–5° C. The reaction mixture was stirred for 30 minutes, and further concentrated sulphuric acid (0.4 cm³) added. The resultant solution, containing 5-bromo-2-fluorobenzenediazonium sulphate, was then added dropwise to a solution of potassium iodide (4.23 g) in water (10 cm³) at a temperature of 5°–6° C.; vigorous effervescence was observed during the addition. When the addition was complete, the reaction mixture was allowed to warm to the ambient temperature (22° C.) and was then extracted twice with diethyl ether. The combined extracts were washed successively with brine and sodium thiosulphate solutions, dried over anhydrous magnesium sulphate, filtered and concentrated by evaporation of the solvent under reduced pressure. The residual oil was purified by flash column chromatography, using a silica gel support and eluting with petroleum ether (boiling range 40°–60° C.) containing 4% by volume diethyl ether, to give 4-bromo-1-fluoro-2-iodobenzene (4.63 g) as a colourless oil.

$^1$H nmr (CDCl₃): 6.95 (dd, 1H); 7.40 (m, 1H); 7.90 (dd, 1H).

Infra red (liquid film): 3090, 1580, 1470, 1370, 1260, 1240, 1230, 1130, 1082, 1070, 1040, 875, 820, 670, 620 cm⁻¹.

EXAMPLE 2

This Example illustrates the preparation of 4-bromo-1-fluoro-2-phenoxybenzene.

A solution of phenol (0.515 g) in N,N-dimethylformamide (10 cm³) was added dropwise to a suspension of sodium hydride (0.329 g) in N,N-dimethylformamide (10 cm³) at a temperature of 0° C. under an inert atmosphere of nitrogen. When the addition was complete, the cooling source was removed and the mixture stirred for 2 hours at the ambient temperature (22° C.). Cuprous chloride (0.452 g) and a solution of 4-bromo-1-fluoro-2-iodobenzene (1.37 g) in N,N-dimethylformamide (10 cm³) were added to the mixture, which was heated at 100° C. for 17 hours; at this time, the reaction mixture was shown by gas liquid chromatography to contain only a small residue of the unreacted starting material. The mixture was cooled and extracted with diethyl ether. The extract was washed twice with water and once with brine, dried over anhydrous magnesium sulphate, filtered and concentrated by evaporation of the solvent under reduced pressure. The residual oil was passed through a short column of silica gel, using petroleum ether (boiling range 40°–60° C.) containing 10% by volume diethyl ether as eluent. Evaporation of the solvent under reduced pressure gave a clear, pale brown oil (0.92 g). Distillation of this oil at reduced pressure (0.03 mmHg) yielded a number of fractions in a boiling range of 50°–80° C. Two of these fractions were shown by thin layer chromatography to contain principally a single reaction product. These two fractions were combined and purified by preparative thin layer chromatography on a silica gel support, using petroleum ether (boiling range 40°–60° C.) as eluent. 4-Bromo- 1-fluoro-2-phenoxybenzene (0.052 g) was obtained as a colourless oil by evaporation of the eluent under reduced pressure.

$^1$H nmr (CDCl₃): 6.9–7.4 (m)

270 MHz $^{13}$C nmr (CDCl₃): 156.46 (s, 1C); 153.33 (d, 1C); 145.10 (d, 1C); 129.91 (s, 2C); 127.21 (d, 1C); 124.20 (s, 1C); 123.94 (s, 1C); 118.31 (d, 1C); 117.97 (s, 2C); 116.34 (d, 1C).

Infra red (liquid film): 3100–3000, 3000–2800, 1600, 1495, 1450, 1405, 1275, 1250, 1220, 1190, 1170, 1120, 1075, 1025, 910, 880, 810, 755, 695, 630 cm⁻¹.

EXAMPLE 3

This Example illustrates the preparation of 4-fluoro-3-phenoxybenzoic acid.

4-Fluoro-3-phenoxybenzaldehyde (15 g) was dissolved in a mixture of carbon tetrachloride (138 cm³) and acetonitrile (138 cm³), and water (207 cm³) was added. Sodium periodate (31.21 g) was added and the mixture stirred vigorously whilst hydrated ruthenium chloride (0.35 g) was added. After two hours of stirring at the ambient temperature, analysis by thin layer chromatography showed some remaining aldehyde. Further sodium periodate (31.21 g) was added and stirring continued for 1 hour, at which time analysis by thin layer chromatography showed no starting material. The mixture was partitioned between dichloromethane and water, and the aqueous phase separated and extracted three further times with dichloromethane. The combined organic layers were dried over anhydrous magnesium sulphate and the solvents evaporated under reduced pressure to give a brown oil, which was dissolved in diethyl ether and shaken with aqueous sodium hydroxide solution to extract the acid as the sodium salt. Acidification of the aqueous solution gave a white solid which was re-extracted with diethyl ether. The ethereal layers were washed with water, dried over anhydrous magnesium sulphate and the solvent evaporated under reduced pressure to give the title compound as a white solid (13.35 g).

$^1$H NMR (CDCl₃) (ppm): 6.8–7.4 (6H,m); 7.6–7.9 (2H,m); 11.9 (1H, broad)

EXAMPLE 4

This Example illustrates the preparation of 4-fluoro-3-phenoxybenzoyl chloride.

4-Fluoro-3-phenoxybenzoic acid (13.35 g) was mixed with thionyl chloride (65 cm³) and the mixture heated at the reflux temperature for 20 minutes. The mixture was cooled and excess thionyl chloride evaporated under reduced pressure to leave the acid chloride as a brown oil (14.87 g). This product was used directly in the method of the following Example.

EXAMPLE 5

This Example illustrates the preparation of 4-bromo-1-fluoro-2-phenoxybenzene.

The sodium salt of 2-pyridinethiol 1-oxide (8.85 g, was suspended in bromotrichloromethane (297 cm³) under an atmosphere of nitrogen in a reaction vessel covered with aluminium foil to exclude light. The stirred mixture was heated to the reflux temperature and a solution of 4-fluoro-3-phenoxybenzoyl chloride (14.87 g) and α, α'-azo-bis-isobutyronitrile (1.67 g) in bromotrichloromethane (297 cm³) was added dropwise to the refluxing mixture over 90 minutes using a syringe pump. Refluxing was continued for a further 1 hour, at which time analysis of a withdrawn sample by gas liquid chromatography showed only a trace of remaining acid chloride.

The mixture was cooled and partitioned between water and dichloromethane. The aqueous layer was separated and extracted twice with dichloromethane. The combined organic layers were washed with brine, dried over anhydrous magnesium sulphate and concentrated by evaporation under reduced pressure to leave a brown oil. Traces of acid and acid chloride were removed by stirring the product in two molar aqueous sodium hydroxide solution for 10 minutes. Acidification of the aqueous solution gave 7.05 g of recovered 4- fluoro-3-phenoxybenzoic acid. The reaction product was extracted from the aqueous solution with diethyl ether, the ether layer dried over anhydrous magnesium sulphate and the solvent evaporated under reduced pressure to give a brown oil. This oil was purified by column chromatography on silica gel, eluting with petroleum ether (boiling range 60°–80° C.) containing 10% by volume diethyl ether. Two products were obtained in separately eluted fractions:

Product A:

$^1$H NMR (CDCl$_3$) (ppm): 8.75 (1H,m); 7.80 (2H,m); 7.40 (1H,m).

GLC retention time: 3.36 minutes.

Identified by mass and NMR spectrometry as 2-(trichloromethylthio)pyridine.

Product B: (5.65 g)

$^1$H NMR (CDCl$^3$) (ppm): 6.95–7.4 (aromatic H, m).

Infra red (liquid film): 1589, 1488, 1269, 1213 cm$^{-1}$ (major peaks only).

Molecular ion: 266/268.

GLC retention time: 4.42 minutes.

Identified as the required 4-bromo-1-fluoro-2-phenoxybenzene.

I claim:

1. A compound of formula:

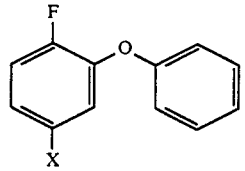

wherein X is selected from bromine and chlorine.

2. 4-Bromo-1-fluoro-2-phenoxybenzene.

3. 4-Chloro-1-fluoro-2-phenoxybenzene.

* * * * *